(12) United States Patent
Sterman et al.

(10) Patent No.: US 6,325,067 B1
(45) Date of Patent: *Dec. 4, 2001

(54) METHODS AND SYSTEMS FOR PERFORMING THORACOSCOPIC CORONARY BYPASS AND OTHER PROCEDURES

(76) Inventors: Wesley D. Sterman, 2121 Sacramento St. #604, San Francisco, CA (US) 94109; Lawrence C. Siegel; Patricia E. Curtis, both of 951 Baileyana Rd., Hillsborough, CA (US) 94010; John H. Stevens, 727 E. Loma Verde Ave., Palo Alto, CA (US) 94303; William S. Peters, 130 Farm Rd., Woodside, CA (US) 94062; Timothy R. Machold, 65 Bernal Ave., Moss Beach, CA (US) 94038

( * ) Notice: Subject to any disclaimer, the term of this patent is extended or adjusted under 35 U.S.C. 154(b) by 0 days.

This patent is subject to a terminal disclaimer.

(21) Appl. No.: 09/482,306

(22) Filed: Jan. 12, 2000

Related U.S. Application Data

(63) Continuation-in-part of application No. 08/023,778, filed on Feb. 22, 1993, now Pat. No. 5,452,733.

(30) Foreign Application Priority Data

Dec. 3, 1992 (AU) .................................................. PL6170

(51) Int. Cl.[7] .................................................. A61B 19/00
(52) U.S. Cl. .............................................................. 128/898
(58) Field of Search .......................... 128/898; 604/500; 623/66, 2.11, 1.11; 606/7, 8

(56) References Cited

U.S. PATENT DOCUMENTS 5,452,733 * 9/1995 Sterman et al. ...................... 128/898
5,735,290 * 4/1998 Sterman et al. ...................... 128/898

* cited by examiner

*Primary Examiner*—David J. Isabella

(57) ABSTRACT

A method for closed-chest cardiac surgical intervention relies on viewing the cardiac region through a thoracoscope or other viewing scope and endovascularly partitioning the patient's arterial system at a location within the ascending aorta. The cardiopulmonary bypass and cardioplegia can be induced, and a variety of surgical procedures performed on the stopped heart using percutaneously introduced tools. The method of the present invention will be particularly suitable for forming coronary artery bypass grafts, where an arterial blood source is created using least invasive surgical techniques, and the arterial source is connected to a target location within a coronary artery while the patient is under cardiopulmonary bypass and cardioplegia

6 Claims, 15 Drawing Sheets

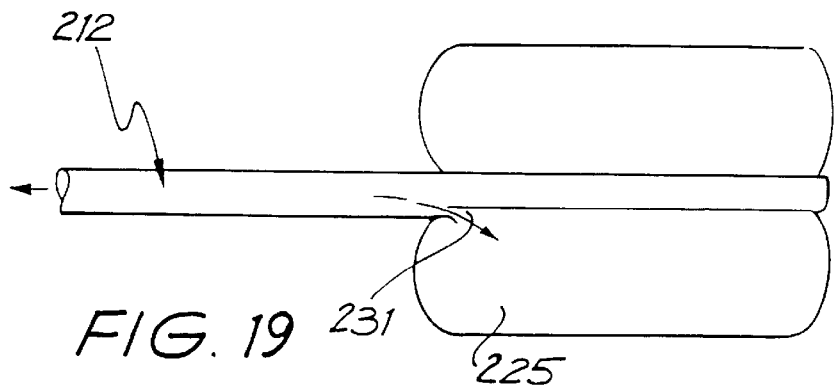
FIG. 19
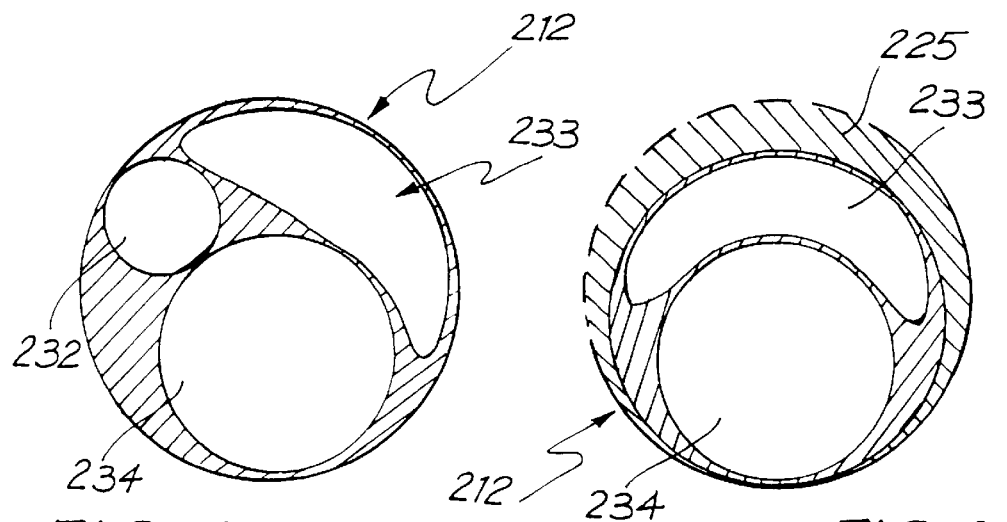
FIG. 20a
FIG. 21
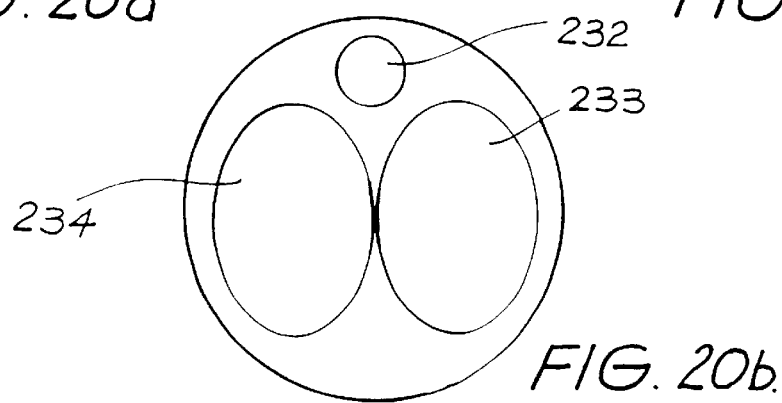
FIG. 20b.

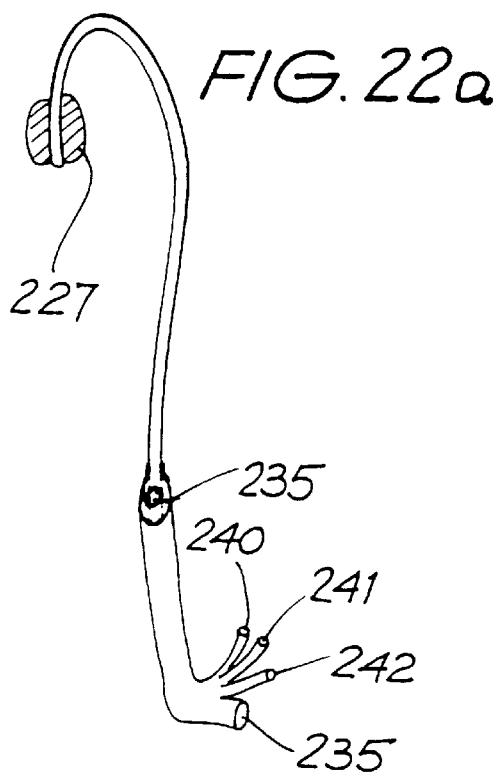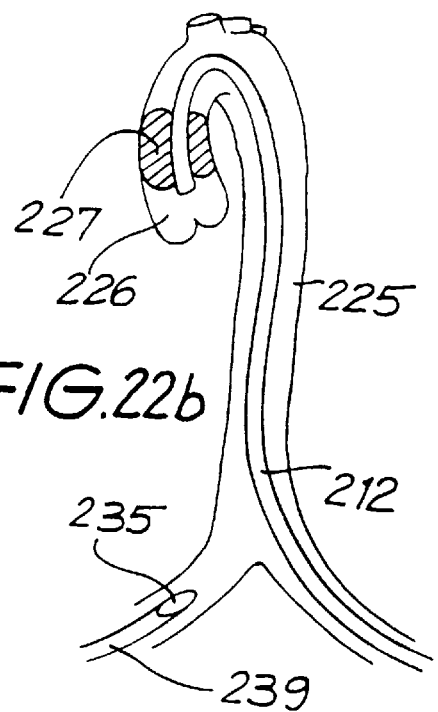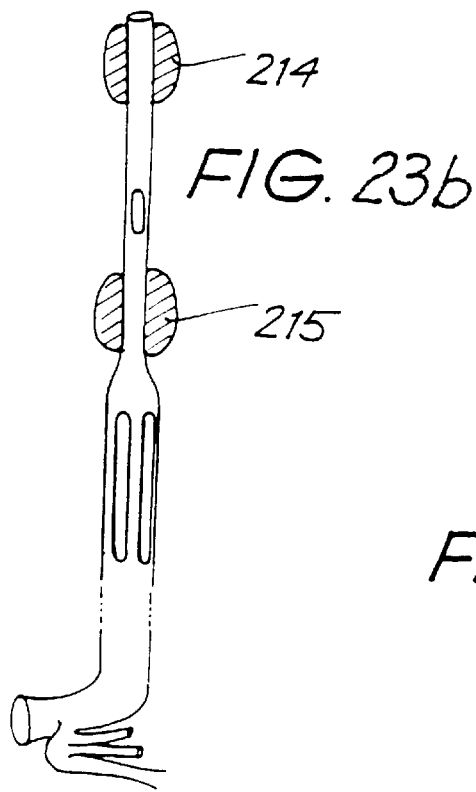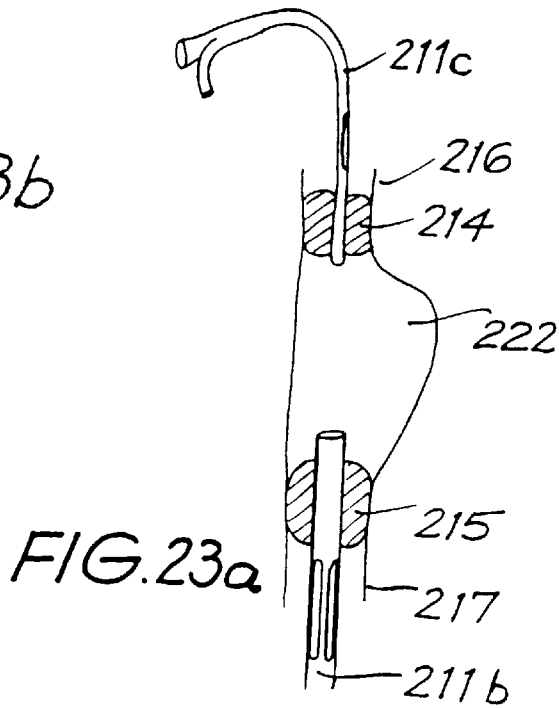

METHODS AND SYSTEMS FOR PERFORMING THORACOSCOPIC CORONARY BYPASS AND OTHER PROCEDURES

CROSS-REFERENCE TO RELATED APPLICATIONS

This application is a continuation-in-part of copending U.S. patent application Ser. No. 08/023,778, filed Feb. 22, 1993 now U.S. Pat. No. 5,452,733, and is related to U.S. patent application Ser. No. 08/159,815, filed Nov. 30, 1993, now abandoned, which is a U.S. counterpart of Australian Patent Application No. PL6170, filed Dec. 3, 1992. The complete disclosures of these related U.S. patent applications are hereby incorporated herein by reference for all purposes.

BACKGROUND OF THE INVENTION

1. Field of the Invention

The present invention relates generally to thoracoscopic methods for performing cardiac procedures. More particularly, the present invention relates to thoracoscopic methods for performing procedures externally on or internally within the heart while the patient s chest is unopened, the patient's heart is stopped, and the patient is supported by cardiopulmonary bypass.

Coronary artery disease remains the leading cause of morbidity and mortality in Western societies. Coronary artery disease is manifested in a number of ways. For example, disease of the coronary arteries can lead to insufficient blood flow resulting in the discomfort and risks of angina and ischemia. In severe cases, acute blockage of coronary blood flow can result in myocardial infarction, leading to immediate death or damage to the myocardial tissue.

A number of approaches have been developed for treating coronary artery disease. In less severe cases, it is often sufficient to treat the symptoms with pharmaceuticals and lifestyle modification to lessen the underlying causes of disease. In more severe cases, the coronary blockage(s) can often be treated endovascularly using techniques such as balloon angioplasty, atherectomy, laser ablation, stents, hot tip probes, and the like.

In cases where pharmaceutical treatment and/or endovascular approaches have failed or are likely to fail, it is often necessary to perform a coronary artery bypass graft procedure using open surgical techniques. Such techniques require that the patient's sternum be opened and the chest be spread apart to provide access to the heart. A source of artenal blood is then connected to a coronary artery downstream from an occlusion while the patient is maintained under cardioplegia and is supported by cardiopulmonary bypass. The source of blood is often the left or right internal mammary artery, and the target coronary artery can be the left anterior descending artery or any other coronary artery which might be narrowed or occluded.

While very effective in many cases, the use of open surgery to perform coronary artery bypass grafting is highly traumatic to the patient. The procedure requires immediate postoperative care in an intensive care unit, a total period of hospitalization of seven to ten days, and a recovery period that can be as long as six to eight weeks.

It would therefore be desirable to provide other, less traumatic methods and techniques for performing coronary artery bypass grafting. It would be particularly desirable if such techniques did not require opening of the patient's sternum, and might be even more desirable it such techniques could be performed using thoracoscopic methods. Such thoracoscopic methods could decrease morbidity and mortality, cost, and recovery time when compared to conventional open surgical coronary bypass procedures. In addition, such methods could be even more efficacious than open-surgical bypass procedures.

2. Description of the Background Art

Conventional thoracoscopic techniques are described in Landreneau et al. (1992) Ann. Thorac. Surg. 54: 800–807. Conventional open surgical procedures for performing coronary artery bypass grafting are described in Kirklin and Barratt Boyes, *Cardiac Surgery*, John Wiley & Sons. Inc. New York 1993 (2nd Ed.). Copending applications Ser. No. 07/730.559, filed Jul. 16, 1991, and Ser. No. 07/991,188, tiled Dec. 15, 1992 now abandoned. Which are assigned to the assignee of the present application, describe catheters that are insertable into a patient's arterial system and include a distal balloon which can be expanded to occlude the ascending aorta. The coronary ostia, the heart, and the proximal ascending aorta may thus be isolated from the remainder of the arterial system while the patient is on cardiopulmonary bypass. Such catheters are particularly intended to be used in heart valve replacement procedures.

SUMMARY OF THE INVENTION

According to the present invention, a method for closed-chest cardiac surgical intervention relies on viewing the region of the heart through a percutaneously positioned viewing scope, such as a thoracoscope, or directly through a small opening between two ribs in the chest. The patient's arterial system will be partitioned during such interventional procedures at a location within the ascending aorta between the brachiocephalic artery and the coronary ostia. In a preferred embodiment, such partitioning is achieved by endovascularly advancing the distal end of a catheter to the desired location with the ascending aorta and expanding a blocking element on the catheter at said location to inhibit the flow of blood and other fluids past said location. Such partitioning facilitates isolation of the heart, and in particular permits the heart to be stopped while the patient is supported by cardiopulmonary bypass. Once the patient's heart is stopped, a variety of surgical procedures can be performed using percutaneously introduced instruments in a minimally invasive fashion. Thus, the present invention contemplates, at least in its preferred embodiments, the possibility of effective ascending aortic occlusion, cardiopiegia, venting, right heart deflation and topical cooling in association with extracorporeal cardiopulmonary by-pass all without necessitating a median sternotomy or other thoracic incision.

In a first aspect the present invention consists in a method for inducing cardioplegic arrest of a heart in situ in a patient's body, comprising the steps of (a) maintaining systemic circulation with peripheral cardiopulmonary by-pass;

(b) occluding the ascending aorta through a percutaneously placed arterial balloon catheter:

(c) introducing a cardioplegic agent into the coronary circulation; and (d) venting the left side of the heart.

The method according to the present invention may be carried out on humans or other mammalian animals. The method is of particular applicability in humans as it allows an alternative approach to open heart surgery and the development of closed cardioscopic surgery. The method according to the invention enables a percutaneous by-pass system to be associated with cardioplegia, venting and cooling of the heart which subverts the need for median sternotomy. This may, in turn, reduce the complications of the surgery.

The maintenance of the systemic circulation involves establishing a cardiopulmonary by-pass. The blood may be drawn into the by-pass merely by positioning a percutaneous catheter into the right atrium and/or into one or both of the vena cavae through which venous blood may be drawn from the heart into an extracorporeal pump oxygenator. In more preferred embodiments of the invention a single catheter with two inflatable cuffs, or two separate catheters, each with an inflatable cuff are introduced into the vena cavae to occlude them adjacent to their right atrial inlets. This allows isolation of the right atrium and allows blood to be drawn from the vena cavae into the by-pass system. There is also preferably provision for percutaneous communication via one catheter with the right atrium to allow infusion of saline into the night atrium. This infusion has the advantage that it allows the heart to be cooled and improves visual acuity within the right heart allowing direct cardioscopic examination and/or intervention.

The catheter used to decompress the right atrium and to draw blood into the by-pass is preferably introduced through the femoral vein by percutaneous puncture or direct cut down. If other than simple venous drainage is required catheters with inflatable cuffs, as described above, are placed preferably such that in inflatable cuff of the cannula is positioned within each of the inferior tsuprahepatic) and superior vena cavae. There is preferably a lumen in the cannula acting as a common blood outlet from the vena cavae leading to the pump oxygenator. A separate lumen is preferably used to infuse saline between the two inflated cuffs into the right atrium. If, alternatively, separate catheters are used to occlude each of the inferior and superior vena cavae than the cannula for the inferior vena cavae is preferably introduced percutaneously from the femoral vein and that for the superior vena cavae is introduced percutaneously through the jugular or subclavian vein.

The ascending aorta is preferably occluded by a balloon catheter introduced percutaneously through the femoral artery. This catheter must carry adjacent its tip an inflatable cuff or balloon of sufficient size that upon being inflated it is able to completely occlude the ascending aorta. The length of the balloon should preferably not be so long as to impede the flow of blood or other solution to the coronary arteries or to the brachiocephalic, left carotid or left subclavian arteries. A balloon length of about 40 mm and diameter of about 35 mm is suitable in humans. The balloon may be of a round, cylindrical, or other appropriate shape to fully and evenly accommodate the lumen of the ascending aorta. This maximizes the surface area contact with the aorta, and allows for even distribution of occlusive pressure.

The balloon of the catheter is preferably inflated with a saline solution to avoid the possibility of introducing into the patient an air embolism in the event that the balloon ruptured. The balloon should be inflated to a pressure sufficient to prevent regurgitation of blood into the aortic root and to prevent migration of the balloon into the root whilst not being so high as to cause damage or dilation to the aortic wall. An intermediate pressure or the order of 350 mmHg, for example, has been proven effective in trials.

The aortic catheter is preferably introduced under fluoroscopic guidance over a suitable guidewire. Transoesophageal echocardiography can alternatively be used for positioning as has been described with reference to the venous catheter. The catheter may serve a number of separate functions and the number of lumina in the catheter will depend upon how many of those functions the catheter is to serve. The catheter can be used to introduce the cardioplegic agent, normally in solution, into the aortic root via one lumen. The luminal diameter will preferably be such that a flow of the order of 250–500 ml/min of cardioplegic solution can be introduced into the aortic root under positive pressure to perfuse adequately the heart by way of the coronary arteries. The same lumen can, by applying negative pressure to the lumen from an outside source, effectively vent the left heart of blood or other solutions. It may also be desirable to introduce medical instruments and/or a cardioscope into the heart through another lumen in the catheter. The lumen should be of a diameter suitable to pass a fibre-optic light camera of no greater than 3 mm diameter. It is however, preferable that the diameter and cross-sectional design of the internal lumina is such that the external diameter of the catheter in its entirety is small enough to allow its introduction into the adult femoral artery by either percutaneous puncture or direct cut-down.

The oxygenated blood returning to the body from the by-pass system may be conveyed into the aorta from another lumen in the cannula carrying the balloon. In this case the returning blood is preferably discarded from the catheter in the external iliac artery. In another embodiment of the invention, and in order to reduce the diameter of the catheter carrvinz the balloon, a separate arterial catheter of known type may be used to return blood to the patient from the by-pass system. In this case a short catheter is positioned in the other femoral artery to provide systemic arterial blood from the by-pass system. The control end of the catheter, i.e. that end that remains outside of the body, should have separate ports of attachment for the lumina. The catheter length should be approximately 900 mm for use in humans.

The cardiopiegic agent may be any of the known materials previously known to be useful, or in the future found to be useful, as cardioplegic agents. The agent is preferably infused as a solution into the aortic root through one of the lumina of the aortic catheter.

In another aspect the present invention consists in a catheter for use in occluding the ascending aorta comprising an elongate tube having one or more continuous lumina along its length, an inflatable cuff is disposed about the tube adjacent one end thereof, the cuff being of such a size that upon being inflated it is able to occlude the ascending aorta to a patient.

The catheter and method according to the present invention can be used to induce cardioplegic arrest and may be used in a number of surgical procedures. These include the following:

(1) Coronary artery revascularization such as
   (a) angioscopic laser introduction or angioscopic balloon angioplasty catheter introduction into the coronary arteries via one lumen of the aortic catheter; or
   (b) thoracoscopic dissection of one or both of the mammary arteries with revascularization achieved by distal anastomoses of the internal mammary arteries to coronary arteries via a small left anterior thoracotomy.
(2) Secundum—type atrial septal defect repair such as by:
   (a) "Closed" cardioscopic or thoracoscopic closure, or
   (b) Closure as an "open" procedure via a mini-right thoracotomy.
(3) Sinus venosus defect repairs or partial anomalous pulmonary venous drainage repairs similar to 2 above.
(4) Infundibular stenosis relief by thoracoscopic or cardioscopic techniques.

(5) Pulmonary valvular stenosis relief by cardioscopic techniques.

(6) Mitral or trianspid valve surgery via a small right thoracotomy, incision, puncture, or trocar.

(7) Aortic stenosis relief by the introduction of instrumentation via a lumen in the aortic catheter into the aortic root.

(8) Left ventricular aneurysm repair via a small left anterior thoracotomy.

The methods of the present invention will be particularly useful for forming coronary artery bypass grafts in a patient suffering from coronary artery disease. The methods will be performed while the treating physician views the region of the heart through the viewing scope, with initial portions of the procedures being performed while normal heart function is maintained. As a first step, the physician will prepare an arterial blood source, typically by harvesting an internal mammary artery or other suitable artery. Conveniently, the lung beneath the internal mammary artery will be collapsed while the other lung remains ventilated. After the arterial blood source is prepared, cardiopulmonary bypass will be established, the patient's arterial system will be partitioned, and the heart stopped, typically by introducing cardioplegic fluid to the isolated heart. A target location on the coronary artery will then be prepared to receive attachment of the arterial blood source, typically by forming an incision at a location downstream from a narrowed region in the artery. The arterial blood source can be connected to the coronary artery by various conventional anastomotic techniques, such as suturing.

The methods of the present invention provide a minimally-invasive approach for forming coronary artery bypass grafts with an efficacy equal to or greater than conventional open surgical bypass techniques. The methods of the present invention can be adapted to create anastomoses of a variety and type similar to those created by open surgical techniques, while greatly reducing patient trauma since there is no need to perform a sternotomy. Moreover, the preferred use of an endovascular catheter to partition the aorta and isolate the heart offers a substantial advantage over open surgical techniques where external clamps are placed on the aorta. External clamps can damage the aorta and may frequently cause the release of emboli from the aortic lumen. Additionally, since the sternum does not need to heal after the procedure, both internal mammary arteries can frequently be used in a single procedure to provide multiple bypass routes. Heretofore, one internal mammary artery was often left in place to provide blood flow to promote healing of the sternum in many open-surgical procedures.

BRIEF DESCRIPTION OF THE DRAWINGS

FIG. 6 further illustrates the connection of a cardiopulmonary bypass system to the patient, as well as the optional placement of a retrograde cardioplegia catheter.

FIG. 19 is a partly cut away side elevationai view of the balloon end of the catheter of FIG. 18 in an inflated condition:

FIG. 20a is a cross-sectional view of the catheter of FIG. 18 intermediate the control end and the balloon end:

FIG. 20b is an alternative cross-sectional arrangement of the lumina in the catheter of FIG. 18:

FIG. 21 is a cross-sectional view through the balloon end of the catheter of FIG. 18:

FIGS. 22a and 22b show schematically two alternative arrangements to the catheter shown in FIG. 18.

FIG. 23a and 23b show schematically two alternative catheter arrangements for the isolation of the right atrium and venous drainage.

DESCRIPTION OF SPECIFIC EMBODIMENTS

The methods of the present invention are suitable for performing a variety of surgical cardiac procedures where the heart will be stopped and the patient supported by cardiopulmonary bypass. The procedures will be minimally invasive and be performed using surgical instruments introduced through a plurality of trocar sheaths placed through the patient's chest. A viewing scope, such as a thoracoscope, will be placed through at least one to the trocar sheaths, and selected surgical instruments will be placed through others of the trocar sheaths and their manipulation viewed by the treating physician using the viewing scope. The term "viewing scope" as used herein is intended to encompass conventional endoscopes, laparoscopes, thoracoscopes, and other video-based visualization devices, as well as other types of devices that facilitate direct or indirect visualization of a body cavity through a small percutaneous penetration. Microscope-based and other types of direct visualization systems which are particularly well-suited for use in the method of the present invention are disclosed in copending applications Ser. No. 08/135,387, filed Oct. 8, 1993 now abandoned, and Ser. No. 08/227,366, filed Apr. 13, 1994, now U.S. Pat. No. 5,588,949 the complete disclosures of which are hereby incorporated herein by reference.

The methods of the present invention are particularly suitable for forming coronary artery bypass grafts, but will also find use in a variety of other procedures. such as mitral valve repair, mitral valve replacement: thrombectomy of the pulmonary artery, left atrium, or left ventricle: removal of atrial myxoma, atrial or ventricular septal defect closure: patent forarnen ovale closure: tricuspid valve annuloplasty: tricuspid valve replacement: ventricular aneurysmectomy: thermal and mechanical cardiac ablation procedures to correct arrhythmias: and the like.

The method of the present invention for performing a coronary artery bypass graft will now be described in detail. The patient undergoing the procedure is prepared in a conventional manner for cardiac surgery. Additionally, both groins are prepared to permit access to the femoral arteries and veins for cardiopulmonary bypass and introduction of the aortic occlusion catheter, as described in more detail hereinafter. The abdomen will also be prepared in case it is necessary to obtain access to an abdominal artery (for example, the gastroepipioic artery) for use in the bypass procedure. The patient is placed under general anesthesia, and a double-lumen endobronchial tube is inserted for selective ventilation or deflation of either lung.

Figure 1:
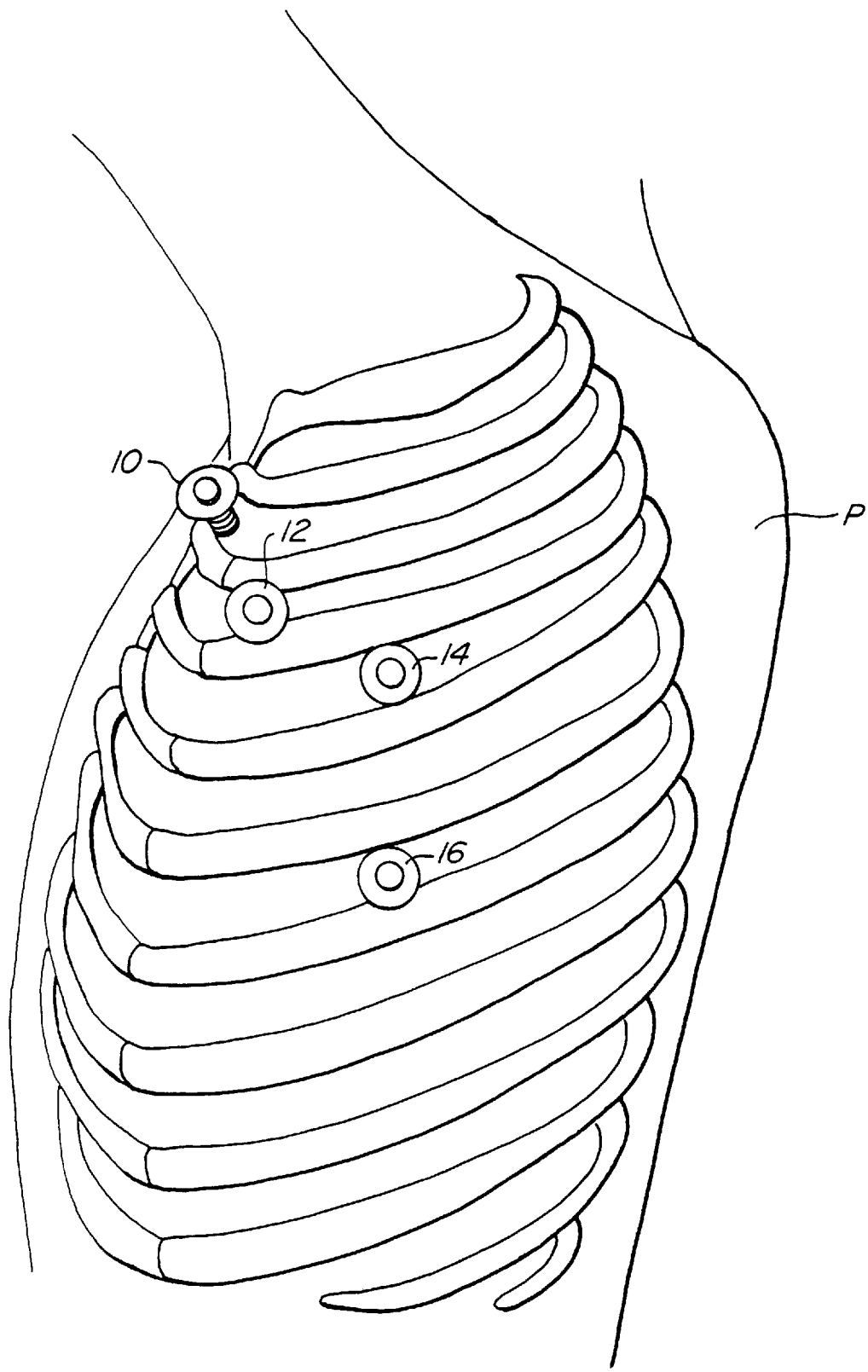
FIG. 1 is a schematic view showing the placement of four trocar sheaths along the lateral chest on the left side of a patient.

After the patient has been prepared as described above, a plurality of access trocar sheaths 10, 12, 14, and 16 will be positioned in the lateral chest of the patient P, as illustrated in FIG. 1. The trocar sheaths of FIG. 1 are shown on the left side of the patient and will be used in the creation of an anastomosis between the patient's left internal mammary artery and the left anterior descending coronary artery, as will be described in detail hereinafter. Note that it will frequently be desirable to have one or more access trocar sheaths in position on the right side of the patient, particularly to permit the introduction of grasping tools to facilitate repositioning the heart, as described in more detail hereinafter. In addition, it may be desirable to position one or more trocar sheaths in parasternal location(s) as well. Usually, one trocar sheath, for example, trocar sheath 12, will be positioned first, and a thoracoscope will be introduced therethrough. The remaining trocar sheaths 10, 14, and 16 can then be positioned based on the relative positions of the coronary arteries and other internal body structures which can be viewed after the thoracoscope has been initially placed.

Figure 2:
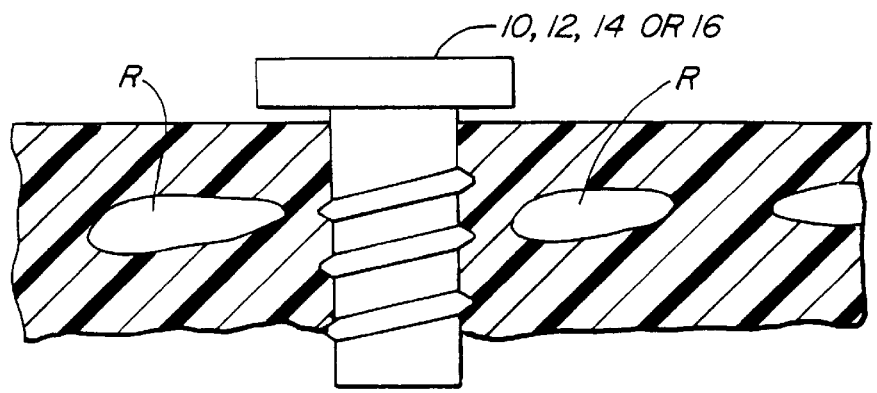
FIG. 2 is a cross-sectional view illustrating the placement of a single trocar sheath between adjacent ribs according to the present invention.

The trocar sheaths 10, 12, 14, and 16 used in the methods of the present invention will generally be shorter than those used for conventional laparoscopic procedures. Typically trocar sheaths useful for the present invention will have a length in the range from about two to 10 cm, and an internal diameter in the range from two to 15 mm. In addition, the trocar sheaths can be flexible to permit manipulation of tools introduced therethrough. As illustrated in FIG. 2, the trocar sheaths will generally be introduced between adjacent ribs R and will penetrate with their caudal aspect lying just above the superior rib surfaces. Suitable thoracoscopic trocar sheaths are available from Snowden-Pencer Corp. under the tradenarne Thora-Port™.

The coronary artery bypass graft procedures of the present invention require that a source of arterial blood be prepared for subsequent bypass connection to the narrowed coronary artery at a location beyond the narrowing. Such arterial blood sources will be primarily of two types. First, existing arteries can be dissected from their natural attachments and transected to provide upstream and downstream free ends. The upstream free end, which is the arterial blood source, will be secured to the coronary artery at a location distal to the narrowing, thus providing the desired bypass blood flow. Second, artificial arterial shunts may be prepared by attaching a natural or synthetic blood vessel, typically a length obtained from a leg vein, at one end to the proximal ascending aorta and at the other end to the target location on a coronary artery. The use of transected arteries is generally preferable since they tend to remain patent for long periods and require only one anastomosis.

The arterial blood source will preferably be the left or right internal mammary artery. It will also be possible to use the gastroepipioic artery in the abdomen. Access to the gastroepiploic artery can be obtained laparoscopically, with the artery being brought into the thorax from the abdominal cavity via a window through the diaphragm. When necessary, it will be possible to prepare free grafts from the aorta. Such free grafts can be formed from veins or arteries harvested from other locations in a patient's body, or may comprise synthetic graft materials. The free graft may be passed into the thorax through either one of the access trocar sheaths or through the aorta (by punching a hole therethrough). The free grafts thus located will be attached at one end to the proximal ascending aorta (to provide the arterial blood supply) and at the other end to the target location on the coronary artery.

The left internal mammary artery is suitable as an arterial source for target locations on the left anterior descending coronary artery, the diagonal coronary artery, the circumflex artery/obtuse marginal artery, and the ramus intermedius coronary artery. The right internal mammary artery is available for connection to all of the same target locations, as well as the right coronary artery and the posterior descending artery. The gastroepiploic artery and free grafts from the aorta will be available for all target locations.

Figure 3:
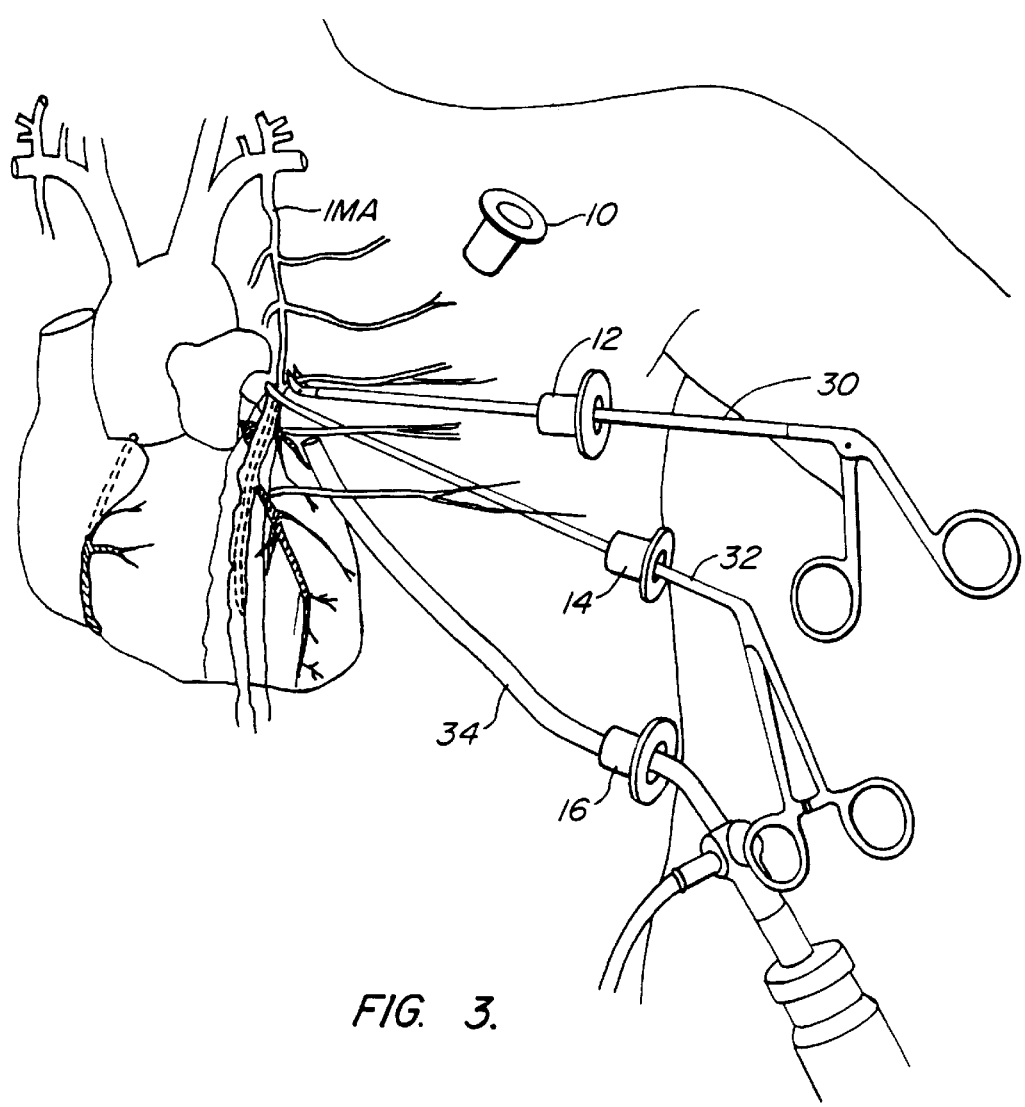
FIG. 3 illustrates the use of an electrosurgical tool introduced through a trocar sheath in order to dissect the left internal mammary artery from the inner thoracic wall to free the artery prior to transection.
Figure 4:
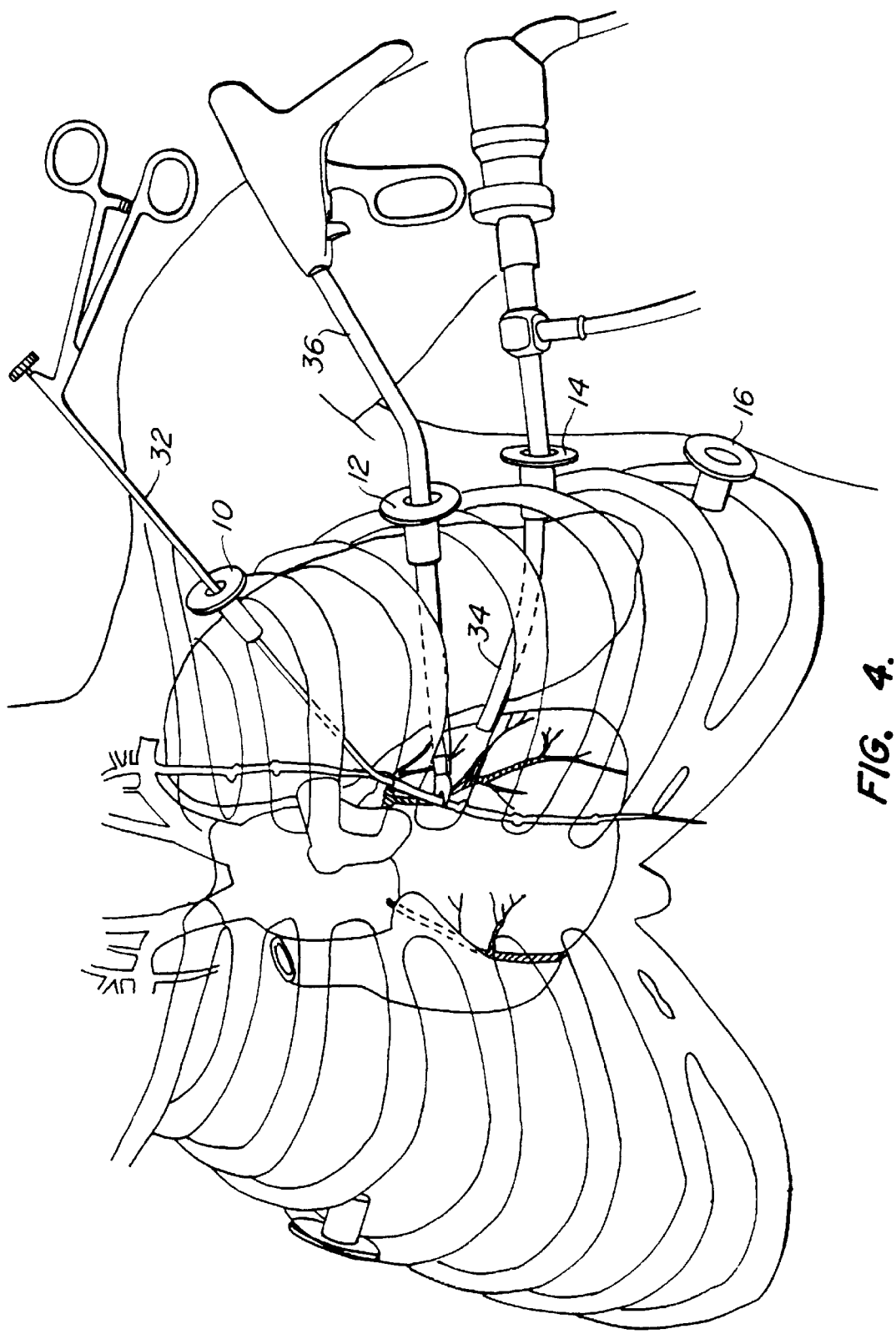
FIG. 4 illustrates the use of a clip applier introduced through a trocar sheath in order to seal off portions of the left internal mammary artery prior to transection.

Referring now to FIGS. 3 and 4, an exemplary procedure according to the present invention for transecting the left internal mammary artery IMA will be described. initially, the left luna is deflated and an electrosurgical tool 30 is used to dissect a length of the internal mammary artery IMA from the inner thoracic wall. The side branches of the internal mammary artery are sealed. The electrosurgical tool 30 is then introduced through trocar sheath 12 while a grasper 32 or other tool for applying tension on the artery IMA is introduced through trocar sheath 14. The thoracoscope 34 may be positioned through the trocar sheath 16 in order to most advantageously view the operating area at this point in the procedure.

Figure 5:
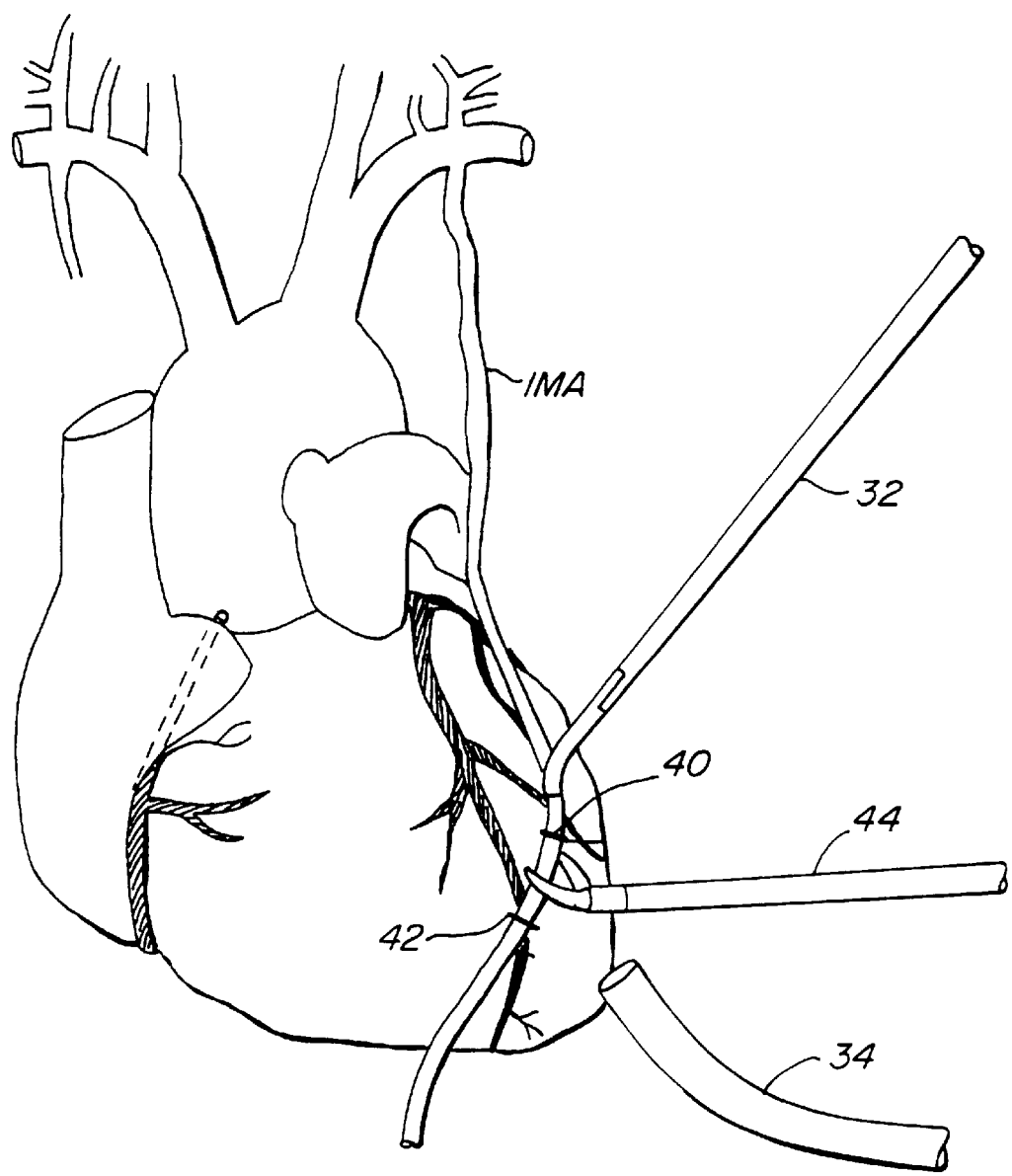
FIG. 5 illustrates transection of the left internal mammary artery to provide an arterial blood source according to the method of the present invention.
Figure 7:
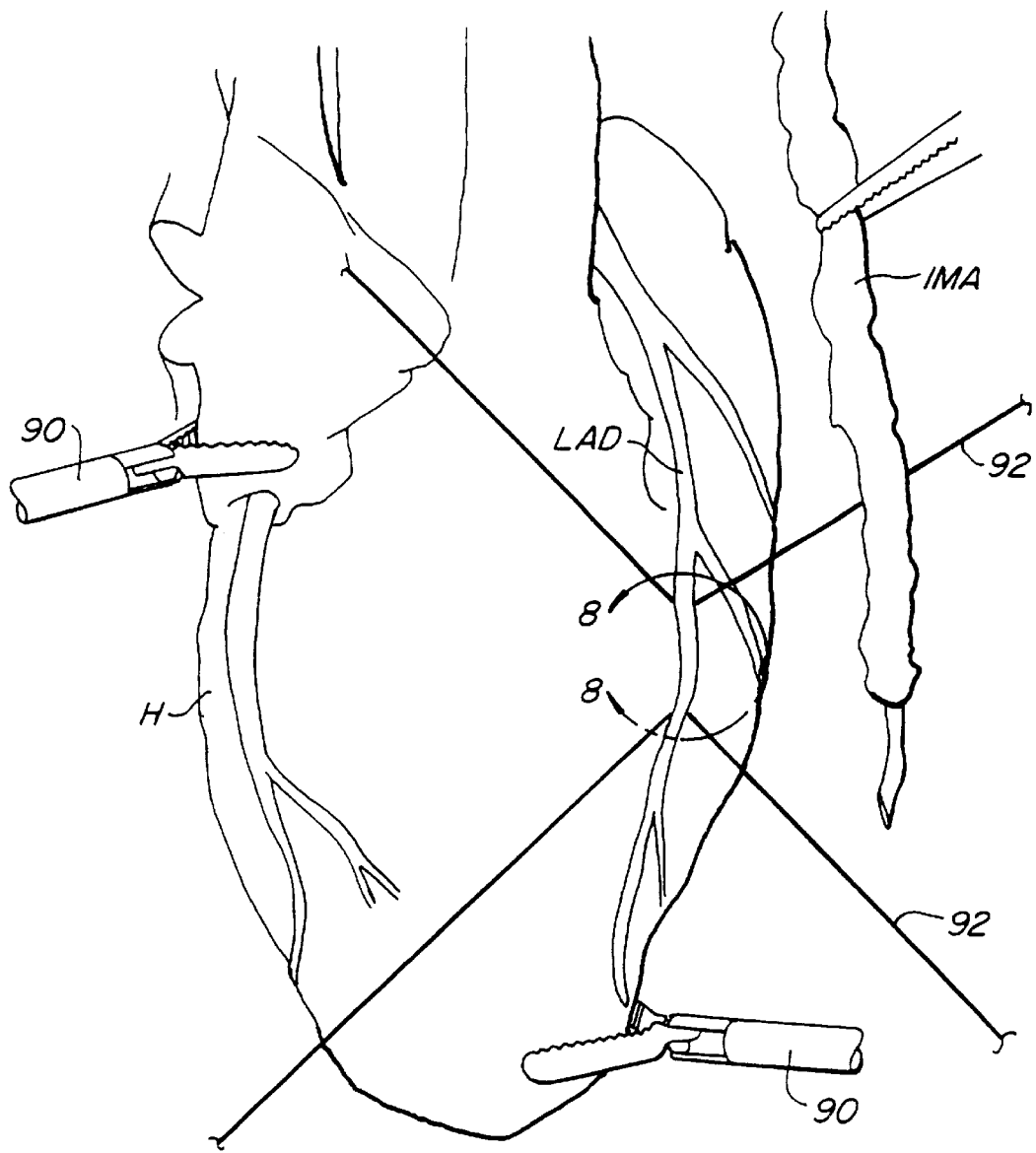
FIG. 7 illustrates the preparation of the heart prior to formation of an arteriotomy in the left anterior descending coronary artery which acts as a target location for connection of the internal mammary artery.
Figure 9:
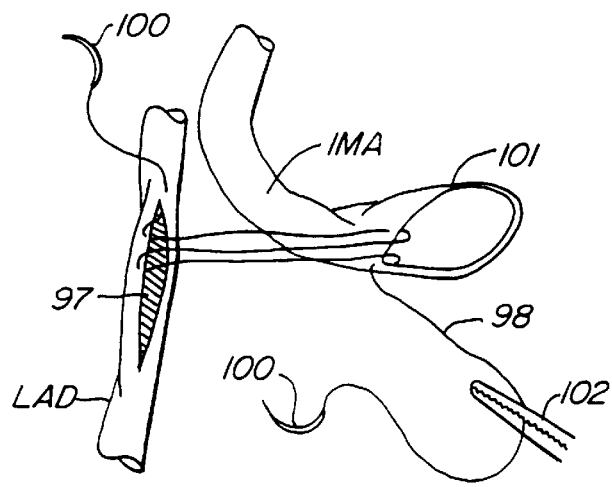
Figure 10:
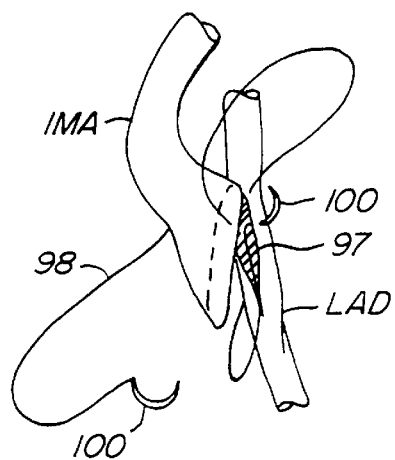
Figure 11:
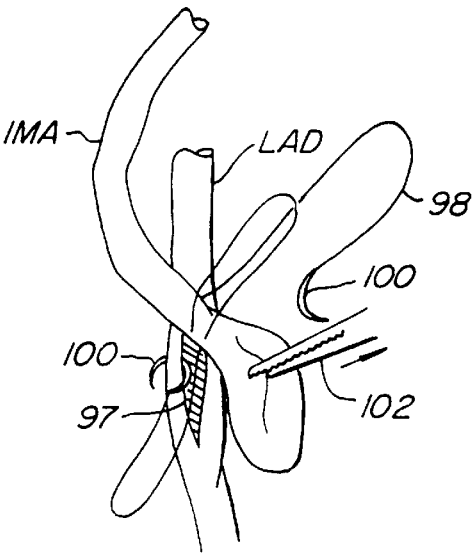
Figure 12:
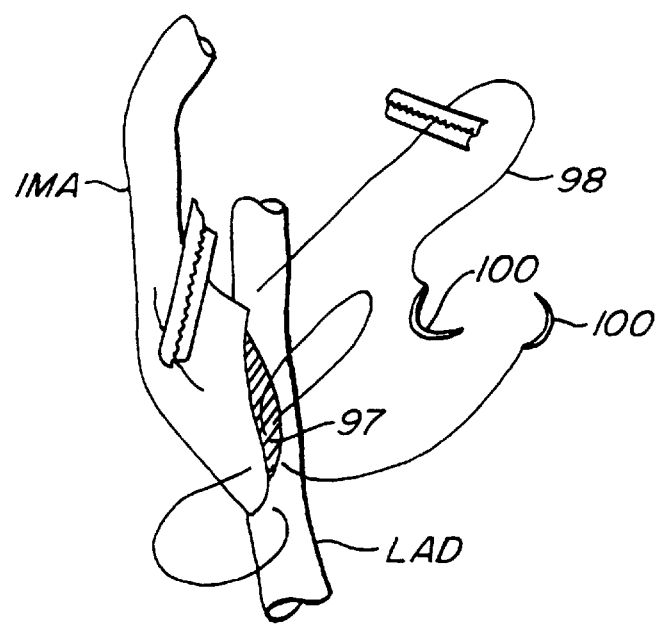
Figure 13:
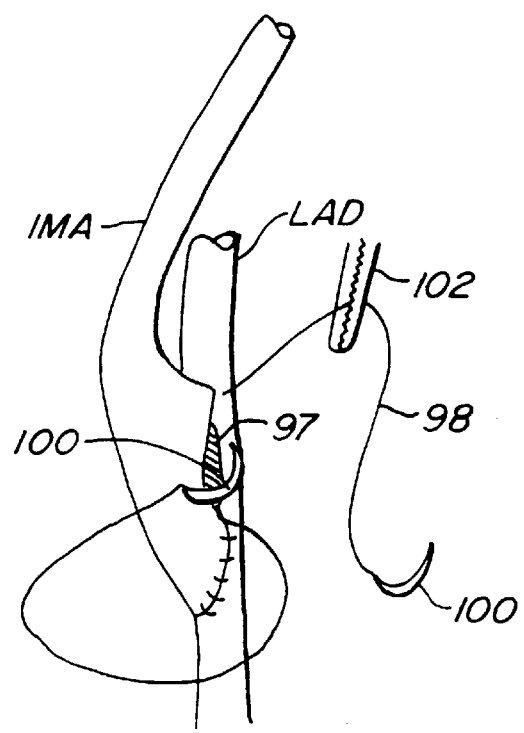

After the internal mammary artery IMA is freed from the thoracic wall, the electrosurgical tool 30 will be replaced with a clip applier 36, with the thoracoscope 34 being moved to trocar sheath 14 and the graspers 32 being moved to trocar sheath 10. The clip applier 36 (FIG. 4) is then used to place one clip 40 upstream and a second clip 42 downstream of a region of the internal mammary artery IMA to be transected, as illustrated in FIG. 5. Upstream clip 40 will be a temporary occlusion device (e.g., a Fogarty clip, Baxter Corp.) which is later removed from the internal mammary artery IMA to establish bypass flow. A removable clip and applicator particularly well-adapted for this procedure are described in copending application Ser. No. 08/265,477 entitled "Endoscopic Vascular Clamping System and Method." filed Jun. 24, 1994, now U.S. Pat. No. 5,564,274 the complete disclosure of which is hereby incorporated herein by reference. Downstream clip 42 will be permanently left in place. After the clips 40 and 42 are applied, a cutting tool 44 can be introduced through the same trocar sheath 12 which had received the clip applying tool, and the cutting tool used to cut the artery in a conventional manner. Note that it will be desirable to cut the artery along a diagonal transverse line in order to provide an oval-shaped distal end, as best seen in FIGS. 7 and 9. If necessary, the original cut can be further trimmed to provide a free upstream end suitable for connection to the narrowed coronary artery at a location distal to the narrowed segment. Usually, excess fat will be dissected from the distal 1–2 cm of the severed artery. The dissection can be carried out either within or outside of the thorax. With outside procedures performed by drawing the upstream free end of the artery out through a trocar sheath temporarily.

While various types of endoscopic surgical instruments may be utilized to isolate, dissect, and clip the IMA, and to attach the IMA to a coronary artery, it is presently preferred to use instruments that are specifically adapted for the highly-precise, thoracoscopic microsurgery which the method of the invention requires. Such instruments must be dimensioned to pass through trocar sheaths positioned within intercostal spaces in the rib cage and to reach the IMA and the heart from outside the chest cavity. In addition, the instruments should have very precise actuators subject to easy and controllable actuation, and end-effectors specifically adapted for IMA isolation, dissection, clipping, and attachment of the IMA to a coronary artery. Thoracoscopic microsurgical instruments specifically designed for carrying out the method of the invention are described in copending application Ser. No. 08/194,946, filed Feb. 11, 1994, the complete disclosure of which is hereby incorporated herein by reference.

A particular advantage of the method of the present invention is that both the left and the right internal mammary arteries can be used for bypass in a single procedure. Moreover, each internal mammary artery can be used to form more than one bypass anastomosis including both side-to-side anastomoses and an end-to-side anastomosis. Either internal mammary artery may be used for revascularizations on either side of the heart.

After the internal mammary artery IMA has been transected and prepared, it is necessary to place the patient on cardiopulmonary bypass and to induce cardioplegia (i.e., stop cardiac contraction) prior to connecting the arterial graft to the coronary artery. Cardioplegia can be induced by introducing certain chemicals (usually potassium-containing solutions) into the interior of the myocardium and requires that the patient's arterial system be partitioned to isolate the heart, coronary arteries, and proximal ascending aorta from the remainder of the patient's vascular system. The isolated heart and ascending aorta can then be selectively exposed to a cold solution that contains a high concentration of cardiopleoic chemicals.

Figure 6:
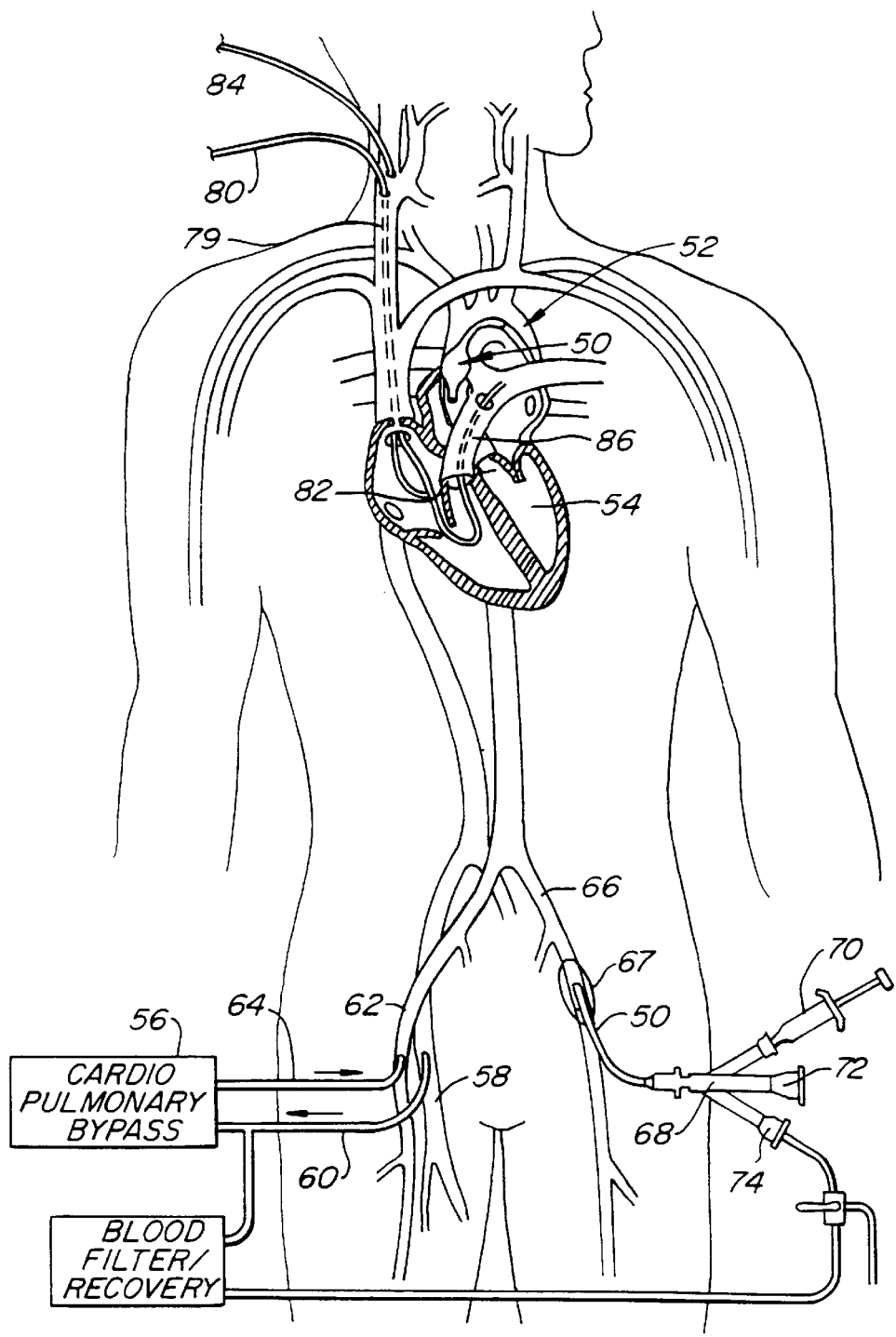
FIG. 6 illustrates the use of an endovascular catheter to partition the patient's heart at a location within the ascending aorta according to the method of the present invention.

Referring to FIG. 6, the arterial system may be partitioned using an aortic occlusion balloon catheter 50 which is positioned in the ascending aorta 52 to separate the left ventricle 54 and proximal portion of the ascending aorta from the rest of the patient's arterial system. A cardiopulmonary bypass system 56 removes venous blood from the femoral vein 58 using a conventional blood withdrawal catheter 60. The bypass system 56 removes carbon dioxide from the blood, oxygenates the blood, and returns the oxygenated blood to the patient's femoral artery 62 through a conventional return catheter 64. The bypass system 56 will operate at a sufficient pressure to drive the circulation of the blood through the patient's arterial system except for that portion which is blocked by the aortic occlusion catheter.

The aortic occlusion catheter 50 is preferably endovascularly introduced over a conventional guidewire to the ascending aorta through the left femoral artery 66 which is entered either percutaneously or through an open cut down 67 of the groin. A proximal hub 68 is located on the proximal end of the occlusion catheter 50 and includes a balloon inflation means, such as syringe 70, and a main access port 72 to permit the introduction of instruments, irrigation fluid, and the like. Optionally, a third introduction port 74 may be provided to receive blood and other fluids vented from the aortic root through catheter 50 and deliver the withdrawn blood to the CPB system (after filtering). Alternatively, blood and other fluids may be vented through main access port 72, with third access port 74 communicating with a separate lumen in catheter 50 having an opening distal to the occlusion balloon for measuring pressure in the aortic root. The provision of access ports in the aortic occlusion catheter 50 is optional. It is necessary only that the catheter 50 be able to position a blocking element, such as the inflatable balloon, at the proper location within the ascending aorta. One or more access ports and lumens, however, may be an advantage in a variety of circumstances. For example, the catheter 50 with an access lumen would permit anterograde administration of cardioplegic fluid and would also permit anterograde venting of the left ventricle. Such a lumen could also provide access by acting as an anchored guiding catheter for a variety of other conventional diagnostic and interventional catheters, such as angiography, angioplasty, atherectomy, and similar vascular catheters. Suitable aortic occlusion catheters having such access ports and lumens are described in detail in copending application Ser. No. 07/991,188, filed on Dec. 15, 1992, now abandoned application Ser. No. 08/123,411, filed Sep. 17, 1993, now abandoned application Ser. No. 08/159,815, filed Nov. 30, 1993, now abandoned application Ser. No. 08/162,742, filed Dec. 3, 1993, now U.S. Pat. No. 5,588,949 and copending application entitled "System for Cardiac Procedures," filed on the same day as the present application, the full disclosures of which are hereby incorporated herein by reference.

As just described, the aortic occlusion balloon catheter 50 will preferably be introduced percutaneously or through an open cutdown of the femoral artery. It may also be possible to introduce the catheter 50 through a trocar sheath placed in the chest, where the catheter is then passed through an aortic arteriotomy in the descending aorta and advanced through the lumen to the location in the ascending aorta, as described above. Introduction via an aortic arteriotomy, however, will generally be less preferred since it is technically more difficult than introduction through the femoral artery. Such introduction, however, may be indicated in cases where the femoral arteries are inaccessible and atherosclerosis of the ascending aorta makes use of an external clamp hazardous (because of possible generation of emboli).

The use of an occlusion catheter 50 having a pre-shaped distal portion may be preferred in some cases to enhance positionability of the balloon in the ascending aorta and to resist displacement. For example, the catheter may have a U-shaped distal portion having a curvature corresponding to that of the aortic arch. To introduce such a device, an obturator having a higher stiffness than that of the catheter may be positioned in the working lumen of the catheter to straighten the shaped distal portion until it is advanced to the aortic arch, at which point the obturator may be withdrawn from the lumen. An aortic occlusion catheter of this type is described in copending application Ser. No. 08/123,411, which has been incorporated herein by reference.

In some cases, the patient's vascular system may be partitioned using an external clamp located on the ascending aorta between the brachiocephalic artery and the coronary ostia. The external clamp would be similar to those employed in open surgical procedures, except that it would be suitable for placement through a trocar sheath under thoracoscopic guidance. Such a thoracoscopic cross-clamp is described in copending application Ser. No. 08/173,899, filed Dec. 27, 1993, which is hereby incorporated herein by reference. Use of an external clamp, however, is generally less preferred since it risks trauma to the aorta, release of emboli from the diseased aortic lumen, and the like.

In addition to provisions for cardiopulmonary bypass and for arterial system partition, the patient will be prepared to receive the introduction of a fluid containing cardiopiegic agents to the myocardium. Such agents may be delivered directly into the aortic root and coronary ostia in an antero-grade manner employing the aortic occlusion catheter for such delivery. The blocking element of the aortic occlusion catheter prevents escape of cardioplegic fluid into the remainder of the arterial circulation.

Alternatively, the cardioplegic agents can be delivered in a retrograde fashion using a coronary sinus catheter 80 which is introduced in a conventional manner through the patient's right internal jugular vein 79, and includes a balloon at the distal end of the catheter extending into the coronary sinus 82. A pulmonary artery venting catheter 84 may also be introduced through the right internal jugular vein 79 and eventually into the pulmonary trunk 86, as illustrated. The pulmonary venting catheter 84 may include an inflatable balloon t not illustrated) which can be used if necessary to occlude the pulmonary trunk 86 as well as an inner lumen which can vent fluid from the pulmonary trunk and thereby decompress the left ventricle 54 as necessary during the procedure. Use of the aortic occlusion catheter 50, the coronary sinus catheter 80, and the pulmonary venting catheter 84 is described more fully in copending application Ser. No. 07/991,188, the disclosure of which has previously been incorporated herein by reference.

Cardiopulmonary bypass and cardioplegia are initiated as follows. First, the cardiopulmonary bypass system 56 is activated, followed by inflation of the blocking balloon on the aortic occlusion catheter. The blocking balloon will be positioned between the brachiocephalic artery and the coronary ostia, neither of which will be occluded. In this way, the patient's left ventricle and proximal ascending aorta are isolated from the distal ascending aorta and the remainder of circulation. Cardioplegic fluid may then be perfused, in either an anterograde or retrograde fashion, into the coronary circulation in order to arrest and cool the heart, while the remainder of the arterial system is perfused with blood, coming from the cardiopulmonary bypass system. Preferably, the temperature of the heart will be lowered to as low as 520 C. by perfusing the heart with cold liquid cardioplegic fluid and optionally by topical cooling. Heart temperature may be monitored using a myocardial probe which is introduced either through one of the trocar sheaths or together with one of the coronary catheters. Such topical cooling may be achieved by infusing cold saline over the heart surface within the pericardium or by covering the heart with a cooling jacket, such as a Dailey jacket available from Medtronic. St. Paul. Minn.

In a preferred embodiment, the cardioplegic fluid consists of an aqueous KCl solution mixed with oxygenated blood at a ratio of four parts blood to one part KCl solution. The aqueous KCl solution consists of crystalloid KCl mixed with saline to have a concentration in the range of 10–50 mEq $K^+$/liter, preferably 15–30 mEq $K^+$/liter. A cooler such as an ice bath (not shown) is used to cool the cardioplegic fluid to e.g. 3° C.–10° C., so as to maintain the heart at a low temperature and to minimize demand for oxygen. This is usually accomplished without applying external cooling to the heart as is generally applied in conventional open cardiac procedures. The cardioplegic fluid is infused into the ascending aorta through an opening at the distal end of occlusion catheter 50 to maintain a pressure in the aortic root distal to the occlusion balloon sufficient to induce flow of fluid into the coronary arteries through the coronary ostia. A pressure of about 60–80 mmHg as measured through a pressure lumen in catheter 50 is usually sufficient. Cardioplegic fluid is preferably delivered at a flowrate of about 250–350 ml/min., so as to deliver a total volume of 750–1000 ml in about 2–4 minutes, although this may vary depending upon patient anatomy, physiological changes such as coronary dilation, and other factors. In pumping the cardioplegic fluid through the lumen in catheter 50, the fluid should be subject to a pump pressure of no more than about 300 mmHg to minimize damage to the blood component of the mixture. Cardioplegic fluid may also be infused in a retrograde manner through the coronary sinus, by means of a catheter (not shown) positioned transluminally through the right internal jugular vein, as described above. Heart contractions will then cease, with circulation to the remainder of the patient's body maintained by the CPB system. Cardioplegic fluid flow to the patient's myocardium is maintained on a periodic basis, e.g., about every 10–20 minutes for 2–4 minutes, so long as the myocardium is to remain paralyzed. A comprehensive description of cardioplegic techniques suitable for use in the method of the invention is found in Buckberg, Strategies and logic of cardiopiegic delivery to prevent, avoid, and reverse ischemic and repeifusion damage, J. Thorac. Cardiovasc. Surg. 1987;93:127–39.

In addition to or instead of infusion of the blood/crystalloid cardioplegic solution, other techniques may be used to arrest heart contractions. A more concentrated crystalloid KCl solution not mixed with blood may be delivered through a lumen in occlusion catheter 50 at higher pressures than with a blood cardioplegic fluid mixture, since without blood in the solution, there is no risk of hemolysis. This allows the inner lumen (as well as the overall catheter shaft) to be of smaller cross-sectional area while still providing the necessary flowrate of fluid into the aortic root. However, the blood cardioplegia technique described above is presently preferred because it is generally believed to provide greater myocardial protection. In another alternative technique, the patient's body may be cooled in a cold-temperature environment or by application of cold-packs to the chest to reduce the temperature of the myocardium sufficiently to induce fibrillation. The myocardium may be cooled directly by infusion of cold fluid such as cold blood or saline through the coronary arteries. Alternatively, electrical fibrillation may be accomplished by delivering electrical signals to the myocardium by means of electrodes placed on the exterior surface of the heart or externally on the chest. However, cardiac arrest by means of fibrillation is generally less desirable than chemical cardiopleigic paralysis because there remains some degree of heart motion which could make surgical intervention more difficult and because there is a significantly higher demand for oxygen, reducing the safety and duration of the procedure.

After cardiopulmonary bypass has been established, both lungs will be deflated in order to maximize visualization of the cardiac region during the remainder of the method. The left ventricle may be vented, if necessary, using the pulmonary artery vent catheter 84 or an aortic root vent catheter (not illustrated) introduced through an access lumen of the aortic occlusion catheter 50. Alternatively, it may be possible to vent either the pulmonary artery, left atrium, or left ventricle using a catheter passed into the thorax through a trocar sheath, where the catheter is then passed directly through the wall of the artery, atrium, or ventricle. Finally, it is possible to vent the left ventricle using only negative pressure applied to the proximal end of the aortic occlusion catheter. which thus acts as an aortic root vent.

As an alternative to the use of chemical cardioplegic fluids, the patient's heart could be "stopped" for purposes of the present procedures by electrically inducing fibrillation. The necessary electrodes could be introduced through selected trocar sheaths, or could be applied externally on the patients chest. See, Aikins (1984) J. Thorac. Cardiovasc. Surg. 88:174, for a description of such techniques. Use of chemical cardioplegia to arrest the heart will generally be preferred, since the cooled, arrested heart will have a much lower oxygen requirement than the fibrillating heart, which reduces the likelihood of intraoperative injury to the heart.

The patient is now ready to have the diseased coronary artery or arteries prepared for anastomoses. Initially, a pericardiotomy is performed to provide access to the coronary arteries. The pericardiotomy can be performed using suitable instruments, such as electrosurgical instruments, introduced through the lateral chest trocar sheaths (FIG. 1) while viewing the region through the thoracoscope or other suitable visualization device. The pericardium can be incised and spread open for access, or portions of the pericardium can be excised and removed from the thoracic cavity.

While it is possible to perform the anastomosis procedure using a commercially-available thoracoscope for video-based visualization, it is presently preferred to utilize a scope or cannula optically coupled to a surgical microscope to provide direct, stereoscopic visualization of the chest cavity. Such systems are described in copending applications Ser. No. 08/135,387, filed Oct. 8, 1993, and Ser. No. 08/227,366, filed Apr. 13, 1994, now U.S. Pat. No. 5,588,949 which have been incorporated herein by reference. As described in those applications, an endoscope or other optical cannula is positioned so that a distal end of the optical cannula is disposed percutaneously in the left anterior chest, usually in the third, fourth, or fifth intercostal space. A surgical microscope is then positioned over the optical cannula (and, in some embodiments, coupled to the optical carnula) so as to allow visualization of the chest cavity through the optical cannula and microscope. It has been found that the direct vision, high image quality, and depth perception provided by such systems offer significant advantages over video-based thoracoscopic vision in performing the highly-precise microsurgery entailed in performing coronary anastomosis. Direct visualization of the anastomosis site may also be accomplished by looking through an incision between the ribs retracted open using suitable instruments. A device such as that disclosed in PCT Application No. PCT/6593/02888, filed Mar. 25, 1993, may also be used.

Referring now to FIG. 7, the decompressed heart H will now be repositioned using suitable instruments in order to better expose the coronary artery which is the target for anastomosis. Suitable tools include hooks, suction catheters, grasping rods, pushing rods, and the like. Gravity can also be used to help position the heart if the patient can be turned appropriately. As illustrated in FIG. 7, a pair of graspers 90 may be used to secure opposite sides of the heart and permit turning of the heart as desired. Optionally, additional trocar sheaths may be introduced at other sites of thoracic access. For example, one or more parasternal punctures, one or more punctures in the midclavicular line, and/or a subxyphoid puncture may be introduced.

As illustrated, the left anterior descending coronary artery LAD is first pulled upward from the surface of the heart H and stretched using a pair of elastic members 92 which are introduced through appropriately positioned trocar sheaths. The elastic members 92 place axiai tension on the region of the coronary artery LAD which is to be prepared for anastomosis. In addition, they provide a bloodless lumen, permitting excellent visualization.

Figure 8:
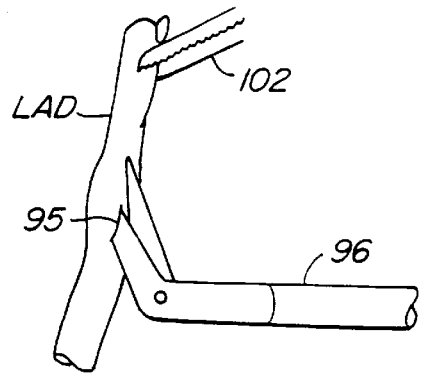
FIGS. 8–13 illustrate the steps of preparing the coronary artery and suturing the internal mammary artery to an incision formed in the coronary artery in order to complete the desired coronary bypass graft. These steps are performed in the region of the coronary artery detailed as circle 8—8 in FIG. 7.

Referring now to FIG. 8, an incision 95 is made in the wall of the coronary artery LAD, where the incision has dimensions selected to match those of the upstream free end of the internal mammary artery graft. The incision 95 is made by first piercing the arterial wall using the tip of a scalpel (not illustrated). Scissors 96 are then introduced through the penetration and used to axially extend the penetration, as illustrated at 97 in FIG. 9.

The internal mammary artery IMA can be joined to the extended incision 97 in the coronary artery LAD by a variety of conventional techniques, including suturing, laser welding, microstapling, and the like. It will be preferred to use conventional suturing techniques as illustrated in FIGS. 9–13. A length of suture 98 has needles 100 at either end, which are manipulated using forceps 102 to join the free upstream end 101 of the internal mammary artery IMA graft to the opening created by the incision 97 in the coronary artery LAD. The instrument designs presently preferred for performing the coronary anastomosis are described in copending application Ser. No. 08/194,946, filed Feb. 11, 1994, the disclosure of which has been incorporated herein by reference.

Figure 14:
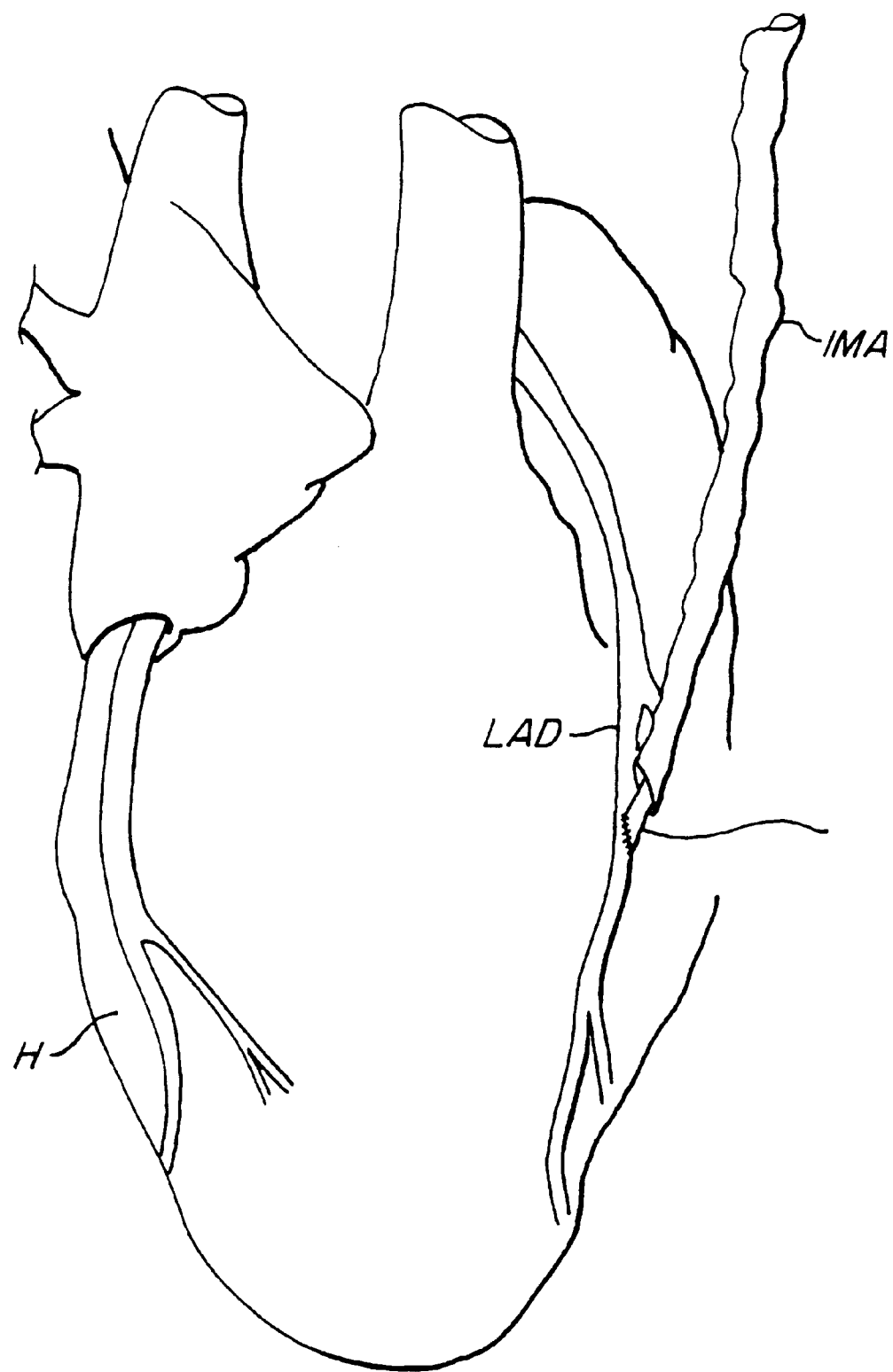
FIG. 14 shows the heart after completion of the coronary artery bypass procedure of the present invention, particularly illustrating the bypass from the left internal mammary artery to the distal left anterior descending coronary artery.

After the suturing is complete, the internal mammary artery IMA will be joined to the coronary artery LAD as illustrated in FIG. 14. The temporary clip 40 will then be removed to permit blood flow from the internal mammary artery IMA into the coronary artery, thus bypassing the previous blockage in the coronary artery. The downstream free end of the internal mammary artery IMA will remain clipped, as described above.

Following completion of the coronary anastomoses, all heart manipulating devices will be removed from the patient, and the heart will be permitted to return to its natural orientation. The aortic occlusion catheter 50 will be deflated. Both lungs will be ventilated, and the coronary arteries will be perfused with blood to initiate cardiac contractions in a conventional manner. If necessary, the heart will be defibriliated to correct its rhythm using electrodes placed either on the heart surface via trocar sheaths or on the patients body surface. The cardiopulmonary bypass will be gradually reduced and stopped. The aortic occlusion catheter will be removed, and the bypass catheters withdrawn. The groin penetrations will be repaired as necessary, all remaining trocar sheaths will be removed, and all thoracic punctures will be sealed in a conventional manner. Finally, the patient will be recovered from anesthesia.

Figure 15:
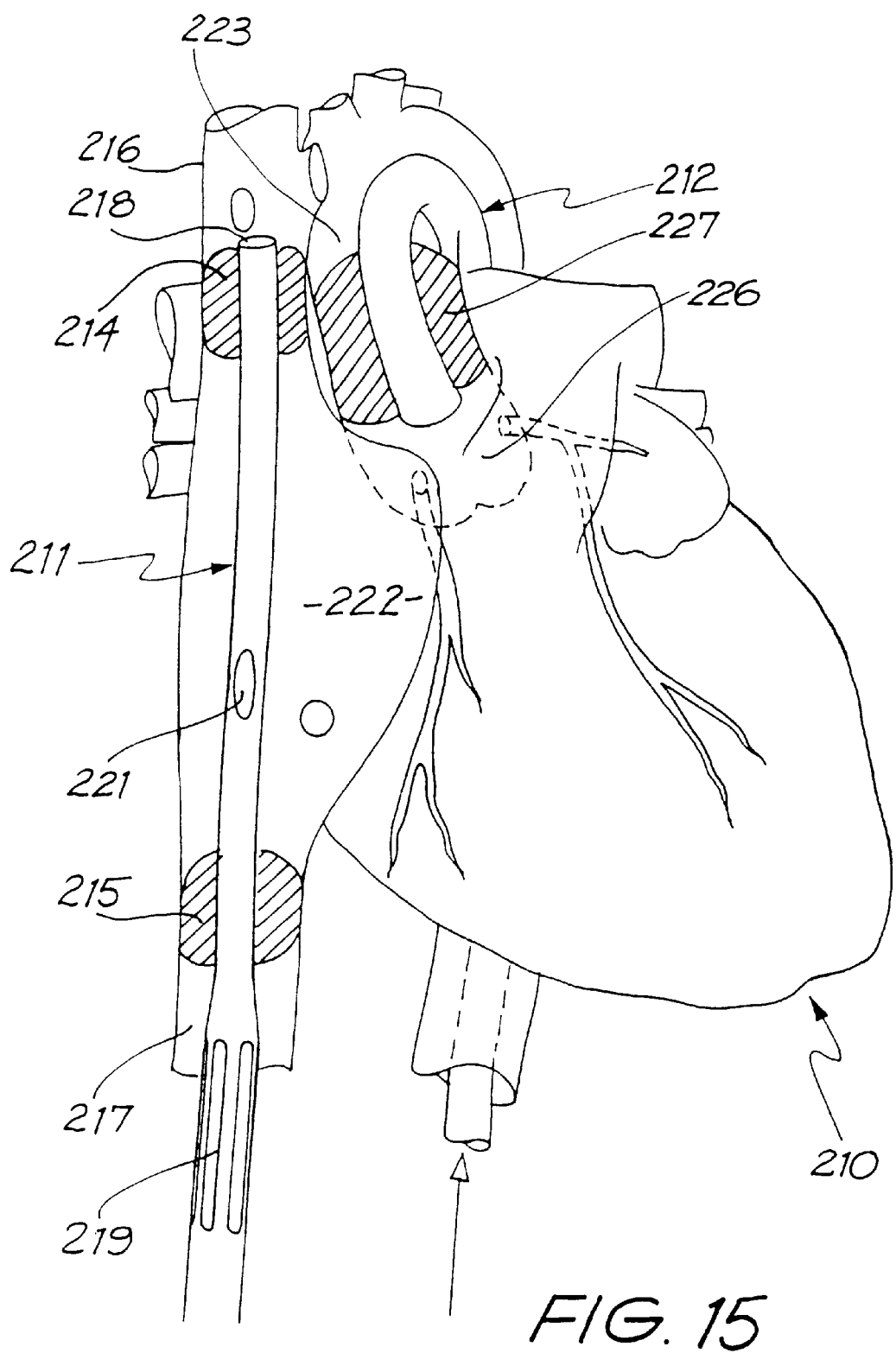
FIG. 15 is a schematic partly cut-away representation of a patient's heart having percutaneous catheters placed therein for carrying out the method according to the present invention.
Figure 16:
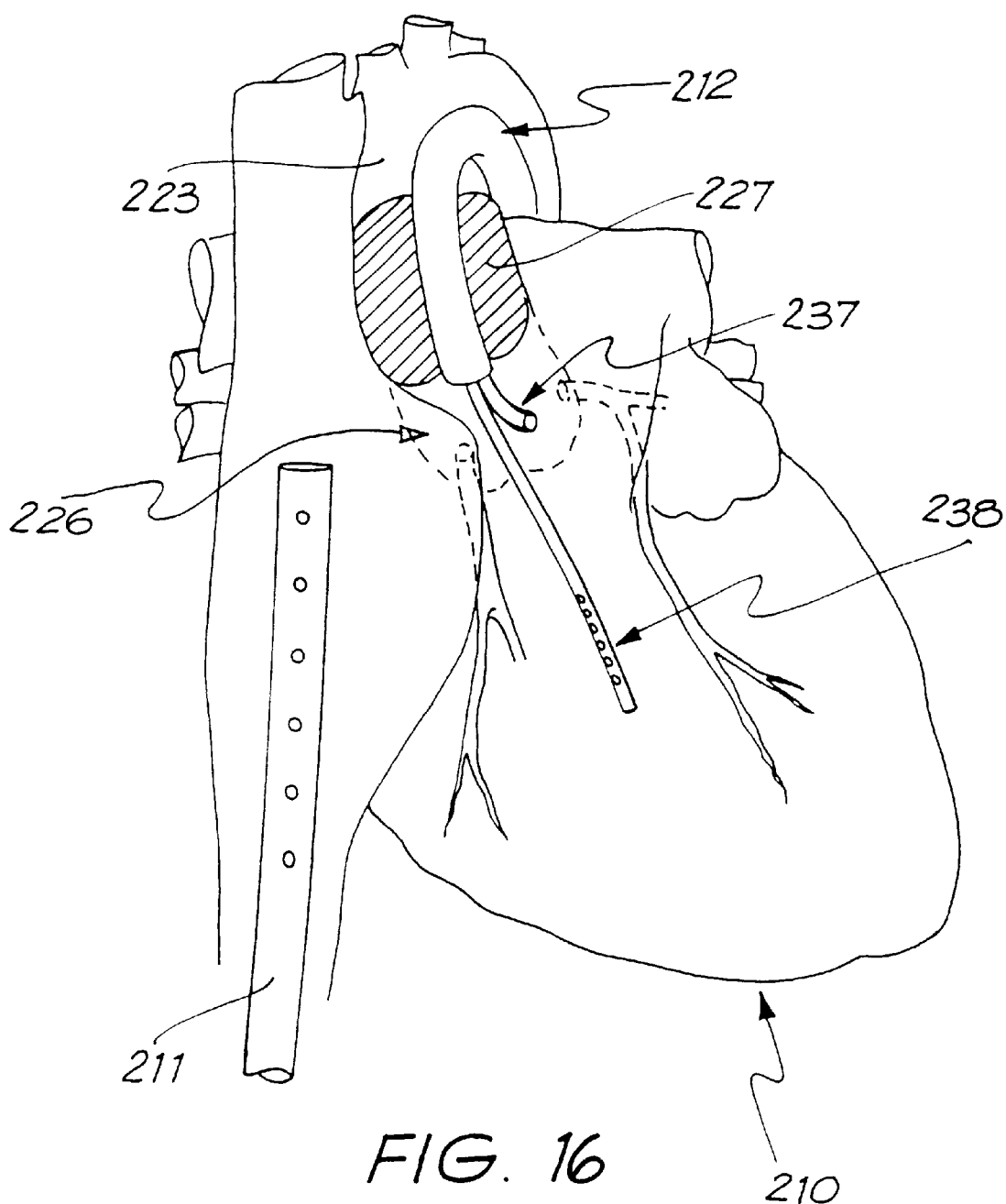
FIG. 16 is a similar view to FIG. 15 showing the aortic catheter in position but including an angioscope and a left ventricular venting cannula introduced into the aortic root and left ventricle respectively, via separate lumina within the aortic catheter.

Additional exemplary embodiments of the endovascular aortic partitioning system of the invention are illustrated in FIGS. 15–23. The heart 210 of FIGS. 15 and 16 is positioned in the living body of a patient and is accessed percutaneously.

In order to induce cardioplegia in the heart while maintaining the patient it is necessary to divert the patient's blood circulation through an extracorporeal cardiopulmonary by-pass system. This is achieved by isolating the heart 210 on both the venous and arterial sides using appropriate percutaneously inserted venous catheter 211, aortic balloon catheter 212, and if this catheter 212 doesn't have provision for arterial blood return, arterial catheter 239 (see FIG. 17). The venous outflow and arterial inflow lumina of the catheters 211 and 212 of the by-pass system are of sufficient cross sectional area to achieve standard blood flows to maintain the patient's systemic circulation during the period of extracorporeal circulation.

In the case of the use of a single venous double-ballooned catheter 211, as is shown in FIG. 15, the catheter 211 is inserted through the femoral vein preferably. A suitable guide wire is initially inserted and the catheter 211 is then introduced in known manner under tluoroscopic guidance. The catheter 211 includes a pair of separately inflatable balloons 214 and 215 each connected to a balloon inflation control device (not shown) through suitable lumina in the catheter 211. The balloon 214 is adapted to occlude the superior vena cavae 216 while the balloon 215 is adapted to occlude the suprahepatic inferior vena cavae 217. A blood withdrawal lumen in the catheter 211 has an inlet orifice 218 flush with the balloon 214, to avoid venous collapse during blood flow into the catheter 211, and a series of inlet slots 219 in the inferior vena cavae. Blood drawn into the inlets 218 and 219 enters a common single lumen. Blood drawn into the by-pass system through the catheter 211 is oxygenated and returned to the patient in a manner which will be hereinafter described.

A separate lumen in the catheter 211 opens into the right atrium 222 through aperture 221 to allow evacuation of blood from the right heart and the infusion of saline to induce topical cooling and/or to improve visual acuity within the right heart.

In use, after the catheter 211 has been positioned the balloons may be inflated or deflated to vary the rate of venous return to the right atrium 222 and therefore the degree of decompression of the left heart. Venous drainage may be effected by gravitational drainage or by applying a degree of negative pressure to assist flow into the pump oxygenator. It will be appreciated that the distance between the balloons 214 and 215 will need to be correct for a given patient and this may be assessed by X-ray examination to allow selection of an appropriately sized catheter. Alternatively separate catheters 211b and 211c could be used, as is shown in FIG. 23a, for the inferior and superior vena cavae, the cannula 211b being introduced as has been described above and the cannula 211c being introduced through the jugular or subclavian vein. It will also be appreciated that for simple operations not requiring complete occlusion of the right atrium it is possible to merely insert a simple catheter 211 into the right atrium to draw blood into the by-pass system as is seen in FIG. 16. Positioning under fluoroscopic guidance is not essential in this case.

Figure 17:
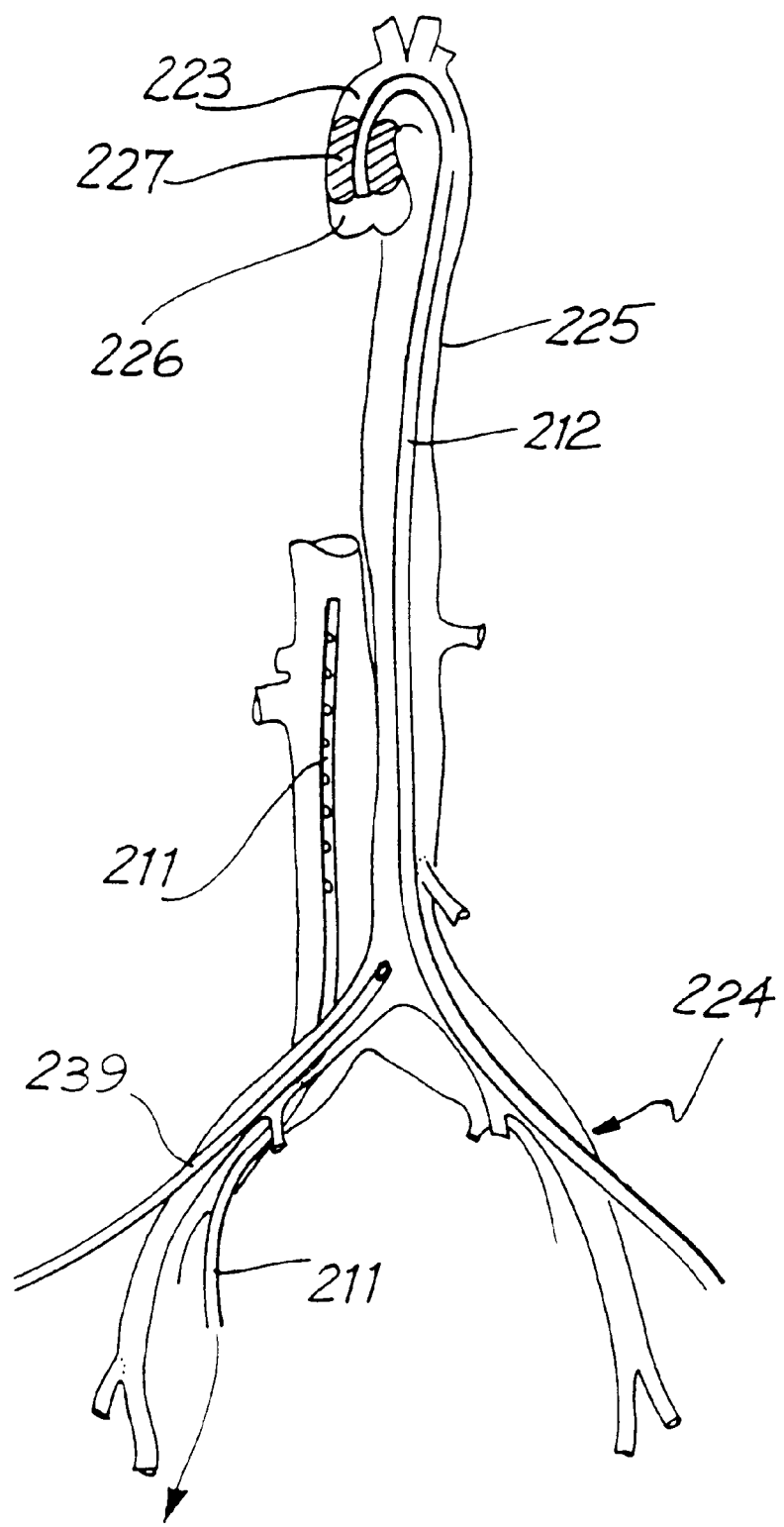
FIG. 17 is a front elevationai view of part of the vascular system of a patient showing, inter alia, the aortic balloon catheter positioned in the ascending aorta via the femoral artery.
Figure 18:
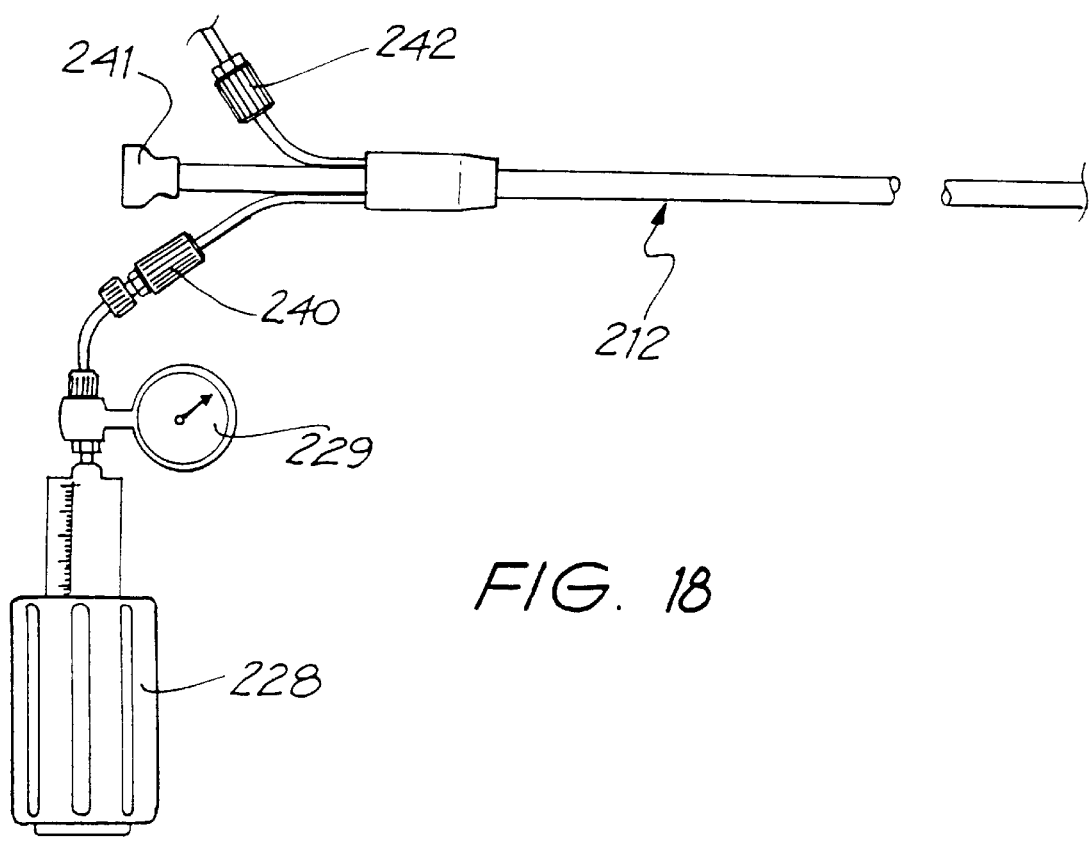
FIG. 18 is a side elevational view of the control end of the aortic catheter according to the present invention.

The catheter 212 is positioned in the manner described above with its free end located in the ascending aorta 223. The catheter 212 is so positioned by insertion preferably through the femoral artery 224 and via the descending aorta 225 as is seen in FIG. 17.

If desired a fluoroscopic dye may be introduced into the aortic root 226 through the catheter 212 for accurate positioning of the tip of the catheter 212 relative to the aortic root 226 and the coronary ostia.

The catheter 212 carries at its free end a balloon 227. The balloon 227 is arranged to be inflated with saline from an inflation control device 228 of known type through a lumen in the catheter 212. The device 228 is fitted with a pressure gauge 229 to allow the operator to control the inflation of the balloon 227. The pressure of the fully inflated balloon 227 should be of the order of 350 mmHg so as to be sufficient to effectively occlude the aorta and to prevent the balloon moving while not being so great as to cause damage to the aortic wall. The balloon 227 should have a maximum diameter sufficient to occlude the aorta and for this purpose the maximum diameter should be about 35 mm. The balloon 227 should have a length of about 40 mm so as not to be so long as to occlude or impede blood flow to the coronary arteries or to the brachiocephalic, subclavian or carotid arteries. If necessary in any given patient the required length and diameter of the balloon may be determined by angiographic, X-ray examination or echocardiography and an appropriately sized catheter selected on that basis.

The balloon 227 is preferably connected to the lumen 232 through which it is inflated at the end of the balloon 227 distal to the tip of the catheter 212 through orifice 231 (see FIG. 19). This allows the tip of the catheter to contain fewer lumina than the remainder of the catheter. Accommodation of the deflated balloon around the tip of the catheter is thus possible without adding to the diameter of the tip as compared with the rest of the catheter 212.

The catheter 212 includes a plurality of lumina (see FIGS. 20 and 21). In addition to the balloon inflation lumen 232 there is at least a single venting/cardioplegia lumen 233 of circular cross-section. There may be a separate and extra circular lumen 234 for instrumentation. If two lumens are present the venting/cardioplegia lumen may be circular or crescent shaped in cross-section (FIG. 20a, 20b). The diameter of the various lumina should be as small as practicable commensurate with the intended use. In addition, there may be a continuous lumen 235 through which arterial blood is returned from the by-pass. This may flow out of the catheter 212 through an orifice in the region of the external iliac artery. In alternative embodiments of the invention such as shown in FIGS. 17 and 22b the arterial return lumen 235 may comprise its own catheter 239 of known type introduced into the other femoral artery or some other suitable artery.

In use the catheter 212 is introduced percutaneously by puncture or cutdown as has been described and once blood flow through the by-pass is established (including systemic cooling) flows are reduced and the balloon 225 is inflated. Flows are then returned to the operating levels and a suitable cardioplegic agent is introduced into the aortic root. Once the full volume of cardioplegic agent has been given and cardiac arrest achieved, the lumen is then used to vent the heart. Venting of the left ventricle may be effected by providing an extended cannula 238 projecting from lumen 233 into the left ventricle (see FIG. 16) or by simply applying negative pressure to the venting lumen 233 of the aortic catheter.

The heart may then be operated on or examined by insertion of instrumentation 237 such as a cardioscope or a laser into the heart through the lumen 234 or through thoracic or atriai trocars. Alternatively, with the heart on by-pass as described above the heart can be approached by an open method by an incision other than median sternotomy.

To reverse cardioplegic arrest the body is rewarmed and the balloon 227 deflated. Aortic blood is thus allowed to perfuse the heart. Whilst the body remains supported by peripheral cardiopulmonary by-pass, the return of the heart rhythm is awaited. External defibrillation may be necessary. Weaning from by-pass is then completed in a routine fashion.

Although the foregoing invention has been described in some detail by way of illustration and example, for purposes of clarity of understanding, it will be obvious that certain changes and modifications may be practiced within the scope of the appended claims.

What is claimed is:

1. A method for forming an anastomosis between a mammary artery and a coronary artery of a patient, said method comprising:

positioning at least one trocar sheath through the patient's chest;

introducing a viewing scope through the trocar sheath to view the region around the heart;

collapsing a lung beneath the mammary artery while ventilating the contralateral lung;

transecting the mammary artery using a tool introduced through a trocar sheath while viewing the artery using the viewing scope;

endovascularly partitioning the patient's arterial system at a location within the ascending aorta between the brachiocephalic artery and the coronary ostia;

establishing cardiopulmonary bypass;

stopping heart contraction;

collapsing both lungs;

forming, an incision in the coronary artery using a cutting tool introduced through a trocar sheath while viewing the artery using the viewing scope while the heart is stopped; and connecting the transected internal mammary artery to the incision in the coronary artery using a tool introduced through one of the trocar sheaths while viewing the arteries using the viewing scope while the heart is stopped.

2. A method as in claim 1, wherein at least three trocar sheaths are positioned on the lateral chest and between adjacent ribs.

3. A method as in claim 1, wherein the internal mammary artery is transected using an electrosurgical cutting tool to dissect the artery from the thoracic wall and a cutting tool to sever the proper length of the artery.

4. A method as in claim 1, wherein the arterial system is partitioned by endovascularly advancing a distal end of a catheter to the location within the ascending aorta, and expanding a blocking element on the catheter at said location to inhibit the flow of blood and other fluids past said location.

5. A method as in claim 1, wherein cardiopulmonary bypass is established from the femoral vein to the femoral artery.

6. A method as in claim 4, wherein the heart is stopped by the anterograde introduction of cardioplegic fluid through the catheter.

* * * * *